(12) United States Patent
Braun et al.

(10) Patent No.: US 9,232,801 B2
(45) Date of Patent: Jan. 12, 2016

(54) 1,2,4-TRIAZINE-3,5-DIONE-6-CARBOXAMIDES AND USE THEREOF AS HERBICIDE

(71) Applicant: BAYER CROPSCIENCE AG, Monheim (DE)

(72) Inventors: Ralf Braun, Ramberg (DE); Christian Waldraff, Bad Vilbel (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/432,378

(22) PCT Filed: Oct. 1, 2013

(86) PCT No.: PCT/EP2013/070424
§ 371 (c)(1),
(2) Date: Mar. 30, 2015

(87) PCT Pub. No.: WO2014/053473
PCT Pub. Date: Apr. 10, 2014

(65) Prior Publication Data
US 2015/0313232 A1    Nov. 5, 2015

(30) Foreign Application Priority Data
Oct. 4, 2012  (EP) .................................... 12187187

(51) Int. Cl.
| | | |
|---|---|---|
| *C07D 403/12* | (2006.01) | |
| *C07D 403/14* | (2006.01) | |
| *C07D 413/12* | (2006.01) | |
| *C07D 413/14* | (2006.01) | |
| *A01N 43/24* | (2006.01) | |
| *A01N 43/647* | (2006.01) | |
| *A01N 43/707* | (2006.01) | |
| *A01N 43/713* | (2006.01) | |
| *A01N 43/82* | (2006.01) | |

(52) U.S. Cl.
CPC .............. *A01N 43/82* (2013.01); *A01N 43/707* (2013.01); *A01N 43/713* (2013.01); *C07D 403/12* (2013.01); *C07D 413/12* (2013.01)

(58) Field of Classification Search
CPC .. C07D 403/06; C07D 403/14; C07D 413/06; C07D 413/14; A01N 43/24; A01N 43/647; A01N 43/707; A01N 43/713
USPC .......................................... 544/182; 514/242
See application file for complete search history.

(56) References Cited

U.S. PATENT DOCUMENTS 8,481,749 B2    7/2013  Braun et al.

FOREIGN PATENT DOCUMENTS

| EP | 1088819 A2 | 4/2001 | | |
|---|---|---|---|---|
| WO | 2012002096 A1 | 1/2012 | | |
| WO | 2012028579 A1 | 3/2012 | | |
| WO | WO 2014126070 A1 * | 8/2014 | ........... | C07D 403/12 |
| WO | WO 2014135654 A1 * | 9/2014 | ........... | C07D 403/12 |

OTHER PUBLICATIONS

International Search Report from corresponding PCT/EP2013/070424, mailed Nov. 19, 2013.

* cited by examiner

*Primary Examiner* — Venkataraman Balasubramanian
(74) *Attorney, Agent, or Firm* — Miles & Stockbridge PC

(57) ABSTRACT

1,2,4-Triazine-3,5-dione-6-carboxamides of the general formula (I) are described as herbicides.

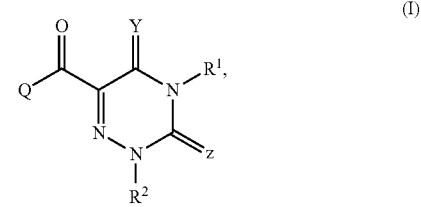

In this formula (I), $R^1$ and $R^2$ are radicals such as hydrogen, organic radicals such as alkyl, and other radicals such as halogen. Q is a tetrazolyl, triazolyl or oxadiazolyl radical. Z and Y are each oxygen or sulfur.

18 Claims, No Drawings

1,2,4-TRIAZINE-3,5-DIONE-6-CARBOXAMIDES AND USE THEREOF AS HERBICIDE

CROSS REFERENCE TO RELATED APPLICATIONS

This application is a §371 National Stage Application of PCT/EP2013/070424, filed 1 Oct. 2013, which claims priority to EP 12187187.5, filed 4 Oct. 2012.

BACKGROUND

1. Field of the Invention

The invention relates to the technical field of the herbicides, especially that of the herbicides for selective control of broad-leaved weeds and weed grasses in crops of useful plants.

2. Description of Related Art

WO2012/002096 A1 discloses, inter alia, 1,2,4-triazine-3,5-dione-6-carbonylcyclohexanediones and 1,2,4-triazine-3,5-dione-6-carbonylpyrazoles as herbicides. However, the compounds known from these documents do not always have adequate herbicidal efficacy and/or compatibility with crop plants.

It has now been found that 1,2,4-triazine-3,5-dione-6-carboxamides are of particularly good suitability as herbicides.

SUMMARY

The present invention therefore provides 1,2,4-triazine-3,5-dione-6-carboxamides of the formula (I), or salts thereof,

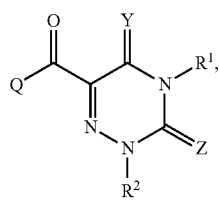

(I)

in which $R^1$ is $(C_1-C_{10})$-alkyl, $(C_2-C_{10})$-alkenyl, $(C_2-C_{10})$-alkynyl, halo-$(C_1-C_{10})$-alkyl, halo-$(C_2-C_{10})$-alkenyl, halo-$(C_2-C_{10})$-alkynyl, $(C_3-C_{10})$-cycloalkyl, halo-$(C_3-C_{10})$-cycloalkyl, $(C_1-C_4)$-alkyl-$(C_3-C_7)$-cycloalkyl, $(C_3-C_7)$-cycloalkyl-$(C_1-C_6)$-alkyl, $(C_3-C_7)$-cycloalkyl-$(C_3-C_7)$-cycloalkyl, halo-$(C_3-C_7)$-cycloalkyl-$(C_1-C_6)$-alkyl, $(C_1-C_6)$-alkyl-$(C_3-C_7)$-cycloalkyl-$(C_1-C_6)$-alkyl, $(C_3-C_{12})$-cycloalkenyl, halo-$(C_3-C_{12})$-cycloalkenyl, $(C_1-C_6)$-alkoxy-$(C_1-C_6)$-alkyl, $(C_1-C_6)$-alkoxy-$(C_2-C_6)$-alkenyl, $(C_1-C_6)$-alkyl-$(C_3-C_7)$-cycloalkyl, $(C_1-C_6)$-alkoxy-$(C_3-C_7)$-cycloalkyl, $(C_3-C_7)$-cycloalkoxy-$(C_1-C_6)$-alkyl, $(C_3-C_7)$-cycloalkoxy-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkylamino-$(C_1-C_6)$-alkyl, di-$(C_1-C_6)$-alkylamino-$(C_1-C_6)$-alkyl, halo-$(C_1-C_6)$-alkylamino-$(C_1-C_6)$-alkyl, $(C_3-C_7)$-cycloalkylamino-$(C_1-C_6)$-alkyl, $(C_1-C_6)$-alkylcarbonyl, halo-$(C_1-C_6)$-alkylcarbonyl, $(C_3-C_7)$-cycloalkylcarbonyl, $(C_1-C_6)$-alkoxycarbonyl, $(C_3-C_7)$-cycloalkoxycarbonyl, $(C_3-C_7)$-cycloalkyl-$(C_1-C_6)$-alkoxycarbonyl, $(C_1-C_6)$-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxyhalo-$(C_1-C_6)$-alkyl, halo-$(C_1-C_6)$-alkoxyhalo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10})$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-C_6)$-alkylamino, halo-$(C_1-C_6)$-alkylamino, halodi-$(C_1-C_6)$-alkylamino, $(C_3-C_{12})$-cycloalkylamino, $(C_1-C_6)$-alkylcarbonylamino, halo-$(C_1-C_6)$-alkylcarbonylamino, $(C_1-C_{10})$-alkylsulfonylamino, halo-$(C_1-C_{10})$-alkylsulfonylamino, $(C_3-C_7)$-cycloalkyl-$(C_1-C_6)$-alkylamino, cyano, hydroxyl, amino, $C(=O)OH$, $C(=O)NHOH$, $SO_2NH_2$, $SO_2NHCN$, $SO_2NHOH$, $NHCHO$, or $R^1$ is phenyl, phenylsulfonyl, $W^1$-(phenyl), $W^1$—(O-phenyl), $W^1$—(S-phenyl), $W^1$—($SO_2$-phenyl), $W^2$—($SO_2CH_2$-phenyl) or $W^2$—($SCH_2$-phenyl), where the phenyl rings of the seven aforementioned radicals each bear s $R^6$ substituents, or $R^1$ is G, $W^2G$ or $W^2OG$, $R^2$ is hydrogen, $(C_1-C_4)$-alkyl, $(C_1-C_4)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, where the phenyl or heteroaryl rings of the four aforementioned radicals each bear s $R^6$ substituents, Q is a $Q^1$, $Q^2$, $Q^3$ or $Q^4$ radical,

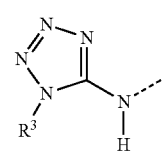

$Q^1$

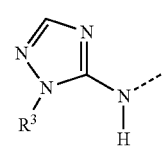

$Q^2$

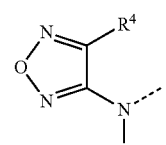

$Q^3$

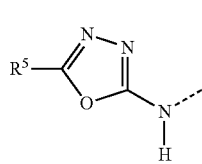

R³ is (C₁-C₈)-alkyl, (C₂-C₈)-alkenyl, (C₂-C₈)-alkynyl, where these radicals are each substituted by s radicals from the group consisting of halogen, cyano, hydroxyl, nitro, SiR¹⁰₃, PO(OR¹⁰)₂, S(O)ₙ—(C₁-C₆)-alkyl, (C₁-C₆)-alkoxy, halo-(C₁-C₆)-alkoxy, COR³ᵃ, COOR³ᵃ, OCOR³ᵃ, NR³ᵃCOR³ᵃ, NR³ᵃSO₂R³ᵇ, (C₃-C₆)-cycloalkyl, heteroaryl, heterocyclyl or phenyl, where the 4 latter radicals are each substituted by p radicals from the group consisting of methyl, ethyl, methoxy, trifluoromethyl, cyano and halogen, and where heterocyclyl bears n oxo groups, or R³ is phenyl substituted by p radicals from the group consisting of halogen, nitro, cyano, (C₁-C₆)-alkyl, halo-(C₁-C₆)-alkyl, (C₃-C₆)-cycloalkyl, S(O)ₙ—(C₁-C₆)-alkyl, (C₁-C₆)-alkoxy, halo-(C₁-C₆)-alkoxy and (C₁-C₆)-alkoxy-(C₁-C₄)-alkyl, R³ᵃ is hydrogen, (C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R³ᵇ is (C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R⁴ is hydrogen, (C₁-C₆)-alkyl, (C₃-C₇)-cycloalkyl, halo-(C₁-C₆)-alkyl, (C₁-C₆)-alkoxy, halo-(C₁-C₆)-alkoxy, (C₂-C₆)-alkenyl, (C₂-C₆)-alkenyloxy, (C₂-C₆)-haloalkenyl, (C₂-C₆)-alkynyl, (C₂-C₆)-alkynyloxy, (C₂-C₆)-haloalkynyl, (C₁-C₆)-alkoxy-(C₁-C₆)-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by p radicals from the group consisting of methyl, ethyl, methoxy, trifluoromethyl and halogen, R⁵ is hydrogen, (C₁-C₆)-alkyl, (C₁-C₆)-alkoxy-(C₁-C₆)-alkyl, CH₂R⁵ᵃ, (C₃-C₇)-cycloalkyl, halo-(C₁-C₆)-alkyl, (C₂-C₆)-alkenyl, halo-(C₂-C₆)-alkenyl, (C₂-C₆)-alkynyl, halo-(C₂-C₆)-alkynyl, OR⁶, NHR⁶, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl or methylsulfonyl, or heteroaryl, heterocyclyl, benzyl or phenyl, each of which is substituted by p radicals from the group consisting of halogen, nitro, cyano, (C₁-C₆)-alkyl, halo-(C₁-C₆)-alkyl, (C₃-C₆)-cycloalkyl, S(O)ₙ—(C₁-C₆)-alkyl, (C₁-C₆)-alkoxy, halo-(C₁-C₆)-alkoxy and (C₁-C₆)-alkoxy-(C₁-C₄)-alkyl, R⁵ᵃ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, (C₁-C₆)-alkoxy or (C₃-C₆)-cycloalkyl, or heteroaryl or heterocyclyl, each of which is substituted by p radicals from the group consisting of methyl, ethyl, methoxy, trifluoromethyl and halogen, Y and Z are each independently O or S, W¹ is (C₁-C₁₀)-alkylene, (C₂-C₆)-alkenylene or (C₂-C₆)-alkynylene, W² is (C₁-C₁₀)-alkylene, G is heteroaryl or heterocyclyl, each of which is substituted by s radicals from the group consisting of halogen, nitro, cyano, (C₁-C₆)-alkyl, halo-(C₁-C₆)-alkyl, (C₃-C₆)-cycloalkyl, S(O)ₙ—(C₁-C₆)-alkyl, (C₁-C₆)-alkoxy, halo-(C₁-C₆)-alkoxy and (C₁-C₆)-alkoxy-(C₁-C₄-alkyl, where heterocyclyl bears n oxo groups, R⁶ is halogen, cyano, hydroxyl, amino, nitro, —CHO, —C(=O)OH, —C(=O)NH₂, —C(=S)NH₂, —C(=O)NHCN, —C(=O)NHOH, —SH, —SO₂NH₂, —SO₂NHCN, —SO₂NHOH, —OCN, —SCN, —SF₅, (C₁-C₆)-alkyl, (C₂-C₆)-alkenyl, (C₂-C₆)-alkynyl, halo-(C₁-C₆)-alkyl, halo-(C₂-C₆)-alkenyl, halo-(C₂-C₆)-alkynyl, (C₃-C₈)-cycloalkyl, halo-(C₃-C₈)-cycloalkyl, (C₁-C₆)-alkyl-(C₃-C₇)-cycloalkyl, (C₃-C₇)-cycloalkyl-(C₁-C₆)-alkyl, (C₃-C₈)-cycloalkenyl, halo-(C₃-C₈)-cycloalkenyl, (C₁-C₆)-alkoxy-(C₁-C₆)-alkyl, (C₃-C₇)-cycloalkoxy-(C₁-C₆)-alkyl, (C₁-C₆)-alkoxy-(C₁-C₆)-alkoxy-(C₁-C₆)-alkyl, (C₁-C₆)-alkylthio-(C₁-C₆)-alkyl, (C₁-C₈)-alkylsulfinyl-(C₁-C₆)-alkyl, (C₁-C₈)-alkoxyhalo-(C₁-C₆)-alkyl, cyano-(C₁-C₆)-alkyl, hydroxy-(C₁-C₆)-alkyl, (C₁-C₆)-alkoxy, halo-(C₁-C₆)-alkoxy, (C₃-C₈)-cycloalkoxy, halo-(C₃-C₈)-cycloalkoxy, (C₃-C₈)-cycloalkyl-(C₁-C₆)-alkoxy, (C₂-C₆)-alkenyloxy, halo-(C₂-C₆)-alkenyloxy, (C₁-C₆)-alkoxy-(C₁-C₆)-alkoxy, (C₂-C₆)-alkylcarbonyloxy, (C₁-C₆)-alkylthio, halo-(C₁-C₆)-alkylthio, (C₃-C₈)-cycloalkylthio, (C₁-C₆)-alkylsulfinyl, halo-(C₁-C₆)-alkylsulfinyl, (C₁-C₆)-alkylsulfonyl, halo-(C₁-C₆)-alkylsulfonyl, (C₃-C₈)-cycloalkylsulfonyl, (C₁-C₆)-alkylamino, di-(C₁-C₆)-alkylamino, halo-(C₁-C₆)-alkylamino, halodi-(C₁-C₈)-alkylamino or (C₃-C₈)-cycloalkylamino, or two vicinal R⁶ radicals form a (C₃-C₆)-alkylene group in which p carbon atoms are replaced by oxygen, sulfur or nitrogen, and in which one carbon atom bears t oxo groups, n is 0, 1 or 2,
p is 0, 1, 2 or 3,
s is 0, 1, 2, 3, 4 or 5,
t is 0 or 1.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may in each case be in any position in the unsaturated radical. Cycloalkyl is a carbocyclic saturated ring system having three to six carbon atoms, for example cyclopropyl, cyclobutyl, cyclopentyl or cyclohexyl.

Analogously, cycloalkenyl is a monocyclic alkenyl group having three to six carbon ring members, for example cyclopropenyl, cyclobutenyl, cyclopentenyl and cyclohexenyl, where the double bond may be in any position. (C₁-C₁₀)-Alkylene is correspondingly a methylene group, an ethylene group, or a propylene, butylene, pentylene, hexylene, heptylene, octylene, nonylene or decylene group, in each case unbranched.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzene ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this is understood to mean that this group is substituted by one or more identical or different radicals from those mentioned. The same applies to the formation of ring systems by different atoms and elements. In this context, the scope of the claims shall exclude those compounds known by the person skilled in the art to be chemically unstable under standard conditions.

According to the type and bonding of the substituents, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers through use of stereoselective reactions using optically active starting materials and/or auxiliaries. The invention also relates to all the stereoisomers and mixtures thereof that are encompassed by the general formula (I) but are not defined specifically. The inventive compounds can also occur as geometric isomers (E/Z isomers) because of the oxime ether structure. The invention also relates to all the E/Z isomers and mixtures thereof that are encompassed by the general formula (I) but are not defined specifically.

The compounds of the formula (I) can form salts. Suitable bases are, for example, organic amines, such as trialkylamines, morpholine, piperidine or pyridine, and also ammonium, alkali metal or alkaline earth metal hydroxides, carbonates and hydrogencarbonates, especially sodium hydroxide and potassium hydroxide, sodium carbonate and potassium carbonate and sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium salts or potassium salts, or else ammonium salts, salts with organic amines or quaternary ammonium salts, for example with cations of the formula $[NRR'R''R''']^+$ in which R to R''' are each independently an organic radical, especially alkyl, aryl, arylalkyl or alkylaryl. Also useful are alkylsulfonium and alkylsulfoxonium salts, such as $(C_1-C_4)$-trialkylsulfonium and $(C_1-C_4)$-trialkylsulfoxonium salts.

The compounds of the formula (I) can form salts through adduct formation of a suitable inorganic or organic acid, for example mineral acids such as HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids such as p-toluenesulfonic acid, with a basic group such as amino, alkylamino, dialkylamino, piperidino, morpholino or pyridino. These salts then contain the conjugate base of the acid as anion.

Preferred compounds of the general formula (I) are those in which $R^1$ is $(C_1-C_{10})$-alkyl, $(C_2-C_{10})$-alkenyl, $(C_2-C_{10})$-alkynyl, halo-$(C_1-C_{10})$-alkyl, halo-$(C_2-C_{10})$-alkenyl, halo-$(C_2-C_{10})$-alkynyl, $(C_3-C_{10})$-cycloalkyl, halo-$(C_3-C_{10})$-cycloalkyl, $(C_1-C_4)$-alkyl-$(C_3-C_7)$-cycloalkyl, $(C_3-C_7)$-cycloalkyl-$(C_1-C_6)$-alkyl, $(C_3-C_7)$-cycloalkyl-$(C_3-C_7)$-cycloalkyl, halo-$(C_3-C_7)$-cycloalkyl-$(C_1-C_6)$-alkyl, $(C_1-C_6)$-alkyl-$(C_3-C_7)$-cycloalkyl-$(C_1-C_6)$-alkyl, $(C_3-C_{12})$-cycloalkenyl, halo-$(C_3-C_{12})$-cycloalkenyl, $(C_1-C_6)$-alkoxy-$(C_1-C_6)$-alkyl, $(C_1-C_6)$-alkoxy-$(C_2-C_6)$-alkenyl, $(C_1-C_6)$-alkyl-$(C_3-C_7)$-cycloalkyl, $(C_1-C_6)$-alkoxy-$(C_3-C_7)$-cycloalkyl, $(C_3-C_7)$-cycloalkoxy-$(C_1-C_6)$-alkyl, $(C_3-C_7)$-cycloalkoxy-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkylamino-$(C_1-C_6)$-alkyl, di-$(C_1-C_6)$-alkylamino-$(C_1-C_6)$-alkyl, halo-$(C_1-C_6)$-alkylamino-$(C_1-C_6)$-alkyl, $(C_3-C_7)$-cycloalkylamino-$(C_1-C_6)$-alkyl, $(C_1-C_6)$-alkylcarbonyl, halo-$(C_1-C_6)$-alkylcarbonyl, $(C_3-C_7)$-cycloalkylcarbonyl, $(C_1-C_6)$-alkoxycarbonyl, $(C_3-C_7)$-cycloalkoxycarbonyl, $(C_3-C_7)$-cycloalkyl-$(C_1-C_6)$-alkoxycarbonyl, $(C_1-C_6)$-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxy-halo-$(C_1-C_6)$-alkyl, halo-$(C_1-C_6)$-alkoxy-halo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10}$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-C_6)$-alkylamino, halo-$(C_1-C_6)$-alkylamino, halodi-$(C_1-C_6)$-alkylamino, $(C_3-C_{12})$-cycloalkylamino, $(C_1-C_6)$-alkylcarbonylamino, halo-$(C_1-C_6)$-alkylcarbonylamino, $(C_1-C_{10})$-alkylsulfonylamino, halo-$(C_1-C_{10})$-alkylsulfonylamino, $(C_3-C_7)$-cycloalkyl-$(C_1-C_6)$-alkylamino, cyano, hydroxyl, amino, C(=O)OH, C(=O)NHOH, $SO_2NH_2$, $SO_2NHCN$, $SO_2NHOH$, NHCHO, or $R^1$ is phenyl, phenylsulfonyl, $W^1$-(phenyl), $W^1$—(O-phenyl), $W^1$—(S-phenyl), $W^1$—($SO_2$-phenyl), $W^2$—($SO_2CH_2$-phenyl) or $W^2$—($SCH_2$-phenyl), where the phenyl rings of the seven aforementioned radicals each bear s R⁶ substituents, or R¹ is G or W²G, R² is hydrogen, (C₁-C₄)-alkyl, (C₁-C₄)-haloalkyl, (C₂-C₆)-alkenyl, (C₂-C₆)-haloalkenyl, (C₂-C₆)-alkynyl, (C₂-C₆)-haloalkynyl, (C₃-C₆)-cycloalkyl, (C₃-C₆)-halocycloalkyl, (C₁-C₆)-alkyl-O—(C₁-C₆)-alkyl, (C₃-C₆)-cycloalkyl-(C₁-C₆)-alkyl, phenyl, phenyl-(C₁-C₆)-alkyl, heteroaryl, (C₁-C₆)-alkylheteroaryl, where the phenyl or hetaryl rings of the four aforementioned radicals each bear s R⁶ substituents, in which Q is a Q¹, Q², Q³ or Q⁴ radical,

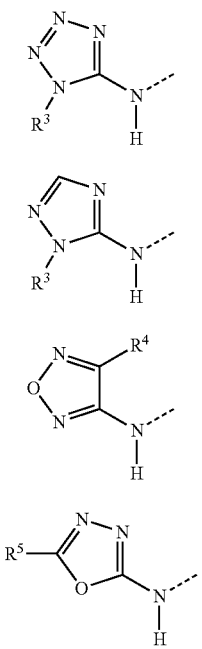

R³ is (C₁-C₈)-alkyl, (C₂-C₈)-alkenyl, (C₂-C₈)-alkynyl, where these radicals are each substituted by s radicals from the group consisting of halogen, cyano, nitro, S(O)ₙ—(C₁-C₆)-alkyl, (C₁-C₆)-alkoxy, halo-(C₁-C₆)-alkoxy, (C₃-C₆)-cycloalkyl, heteroaryl, heterocyclyl or phenyl, where the 4 latter radicals are each substituted by p radicals from the group consisting of methyl, ethyl, methoxy, trifluoromethyl, cyano and halogen, and where heterocyclyl bears n oxo groups, or R³ is phenyl substituted in each case by p radicals from the group consisting of halogen, nitro, cyano, (C₁-C₆)-alkyl, halo-(C₁-C₆)-alkyl, (C₃-C₆)-cycloalkyl, S(O)ₙ—(C₁-C₆)-alkyl, (C₁-C₆)-alkoxy, halo-(C₁-C₆)-alkoxy and (C₁-C₆)-alkoxy-(C₁-C₄)-alkyl, R⁴ is (C₁-C₆)-alkyl, (C₃-C₇)-cycloalkyl, halo-(C₁-C₆)-alkyl, (C₁-C₆)-alkoxy, halo-(C₁-C₆)-alkoxy, cyano, nitro, methylsulfenyl, methylsulfinyl, methylsulfonyl, (C₁-C₄)-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl or piperidin-1-yl, or phenyl in each case substituted by p radicals from the group consisting of methyl, ethyl, methoxy, trifluoromethyl and halogen, R⁵ is hydrogen, (C₁-C₆)-alkyl, (C₃-C₇)-cycloalkyl, halo-(C₁-C₆)-alkyl, (C₃-C₇)-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, R⁶ is halogen, cyano, hydroxyl, amino, nitro, —CHO, —C(=O)OH, —C(=O)NH₂, —C(=S)NH₂, —C(=O)NHCN, —C(=O)NHOH, —SH, —SO₂NH₂, —SO₂NHCN, —SO₂NHOH, —OCN, —SCN, —SF₅, (C₁-C₆)-alkyl, (C₂-C₆)-alkenyl, (C₂-C₆)-alkynyl, halo-(C₁-C₆)-alkyl, halo-(C₂-C₆)-alkenyl, halo-(C₂-C₆)-alkynyl, (C₃-C₈)-cycloalkyl, halo-(C₃-C₈)-cycloalkyl, (C₁-C₆)-alkyl-(C₃-C₇)-cycloalkyl, (C₃-C₇)-cycloalkyl-(C₁-C₆)-alkyl, (C₃-C₈)-cycloalkenyl, halo-(C₃-C₈)-cycloalkenyl, (C₁-C₆)-alkoxy-(C₁-C₆)-alkyl, (C₃-C₇)-cycloalkoxy-(C₁-C₆)-alkyl, (C₁-C₆)-alkoxy-(C₁-C₆)-alkoxy-(C₁-C₆)-alkyl, (C₁-C₆)-alkylthio-(C₁-C₆)-alkyl, (C₁-C₈)-alkylsulfinyl-(C₁-C₆)-alkyl, (C₁-C₈)-alkoxyhalo-(C₁-C₆)-alkyl, cyano-(C₁-C₆)-alkyl, hydroxy-(C₁-C₆)-alkyl, (C₁-C₆)-alkoxy, halo-(C₁-C₆)-alkoxy, (C₃-C₈)-cycloalkoxy, halo-(C₃-C₈)-cycloalkoxy, (C₃-C₈)-cycloalkyl-(C₁-C₆)-alkoxy, (C₂-C₆)-alkenyloxy, halo-(C₂-C₆)-alkenyloxy, (C₁-C₆)-alkoxy-(C₁-C₆)-alkoxy, (C₂-C₆)-alkylcarbonyloxy, (C₁-C₆)-alkylthio, halo-(C₁-C₆)-alkylthio, (C₃-C₈)-cycloalkylthio, (C₁-C₆)-alkylsulfinyl, halo-(C₁-C₆)-alkylsulfinyl, (C₁-C₆)-alkylsulfonyl, halo-(C₁-C₆)-alkylsulfonyl, (C₃-C₈)-cycloalkylsulfonyl, (C₁-C₆)-alkylamino, di-(C₁-C₆)-alkylamino, halo-(C₁-C₆)-alkylamino, halodi-(C₁-C₈)-alkylamino or (C₃-C₈)-cycloalkylamino, or two vicinal R⁶ radicals form a (C₃-C₆)-alkylene group in which p carbon atoms are replaced by oxygen, sulfur or nitrogen, and in which one carbon atom bears t oxo groups, Y and Z are each independently O or S, W¹ is (C₁-C₁₀)-alkylene, (C₂-C₆)-alkenylene or (C₂-C₆)-alkynylene, W² is (C₁-C₁₀)-alkylene, G is heteroaryl or heterocyclyl, each of which is substituted by s radicals from the group consisting of halogen, nitro, cyano, (C₁-C₆)-alkyl, halo-(C₁-C₆)-alkyl, (C₃-C₆)-cycloalkyl, S(O)ₙ—(C₁-C₆)-alkyl, (C₁-C₆)-alkoxy, halo-(C₁-C₆)-alkoxy and (C₁-C₆)-alkoxy-(C₁-C₄)-alkyl, where heterocyclyl bears n oxo groups, n is 0, 1 or 2, p is 0, 1, 2 or 3, s is 0, 1, 2, 3, 4 or 5, t is 0 or 1.

Particularly preferred compounds of the general formula (I) are those in which

R¹ is (C₁-C₁₀)-alkyl, (C₂-C₁₀)-alkenyl, (C₂-C₁₀)-alkynyl, halo-(C₁-C₁₀)-alkyl, halo-(C₂-C₁₀)-alkenyl, halo-(C₂-C₁₀)-alkynyl, (C₃-C₁₀)-cycloalkyl, halo-(C₃-C₁₀)-cycloalkyl, (C₁-C₄)-alkyl-(C₃-C₇)-cycloalkyl, (C₃-C₇)-cycloalkyl-(C₁-C₆)-alkyl, (C₃-C₇)-cycloalkyl-(C₃-C₇)-cycloalkyl, halo-(C₃-C₇)-cycloalkyl-(C₁-C₆)-alkyl, (C₁-C₆)-alkyl-(C₃-C₇)-cycloalkyl-(C₁-C₆)-alkyl, (C₃-C₁₂)-cycloalkenyl, halo-(C₃-C₁₂)-cycloalkenyl, (C₁-C₆)-alkoxy-(C₁-C₆)-alkyl, (C₁-C₆)-alkoxy-(C₂-C₆)-alkenyl, (C₁-C₆)-alkyl-(C₃-C₇)-cycloalkyl, (C₁-C₆)-alkoxy-(C₃-C₇)-cycloalkyl, (C₃-C₇)-cycloalkoxy-(C₁-C₆)-alkyl, (C₃-C₇)-cycloalkoxy-(C₁-C₆)-alkoxy-(C₁-C₆)-alkyl, (C₁-C₆)-alkoxy-(C₁-C₆)-alkoxy-(C₁-C₆)-alkyl, (C₁-C₆)-alkylthio-(C₁-C₆)-alkyl, (C₁-C₆)-alkylsulfinyl-(C₁-C₆)-alkyl, (C₁-C₆)-alkylsulfonyl-(C₁-C₆)-alkyl, (C₁-C₆)-alkylamino-(C₁-C₆)-alkyl, di-(C₁-C₆)-alkylamino-(C₁-C₆)-alkyl, halo-(C₁-C₆)-alkylamino-(C₁-C₆)-alkyl, (C₃-C₇)-cycloalkylamino-(C₁-C₆)-alkyl, (C₁-C₆)-alkylcarbonyl, halo-(C₁-C₆)-alkylcarbonyl, (C₃-C₇)-cycloalkylcarbonyl, (C₁-C₆)-alkoxycarbonyl, (C₃-C₇)-cycloalkoxycarbonyl, (C₃-C₇)-cycloalkyl-(C₁-C₆)-alkoxycarbonyl, (C₁-C₆)-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxy-halo-$(C_1-C_6)$-alkyl, halo-$(C_1-C_6)$-alkoxy-halo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10})$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-C_6)$-alkylamino, halo-$(C_1-C_6)$-alkylamino, halo-di-$(C_1-C_6)$-alkylamino, $(C_3-C_{12})$-cycloalkylamino, $(C_1-C_6)$-alkylcarbonylamino, halo-$(C_1-C_6)$-alkylcarbonylamino, $(C_1-C_{10})$-alkylsulfonylamino, halo-$(C_1-C_{10})$-alkylsulfonylamino, $(C_3-C_7)$-cycloalkyl-$(C_1-C_6)$-alkylamino, cyano, hydroxyl, amino, C(=O)OH, C(=O)NHOH, SO$_2$NH$_2$, SO$_2$NHCN, SO$_2$NHOH, NHCHO, or $R^1$ is phenyl, $W^1$-(phenyl), where the phenyl rings each bear s $R^6$ substituents, or $R^1$ is G, $R^2$ is $(C_1-C_4)$-alkyl, $(C_1-C_4)$-haloalkyl, phenyl, heteroaryl, where the phenyl or heteroaryl rings in the two aforementioned radicals each bear s $R^6$ substituents, Q is a $Q^1$, $Q^2$, $Q^3$ or $Q^4$ radical,

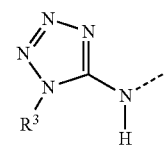
$Q^1$

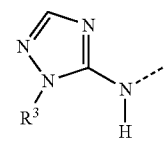
$Q^2$

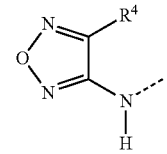
$Q^3$

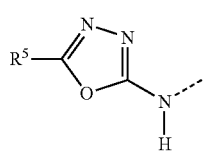
$Q^4$ $R^3$ is $(C_1-C_8)$-alkyl, $(C_2-C_8)$-alkenyl or $(C_2-C_8)$-alkynyl, each of which is substituted by s radicals from the group consisting of halogen, cyano, nitro, $S(O)_n$—$(C_1-C_6)$-alkyl, $(C_1-C_6)$-alkoxy and halo-$(C_1-C_6)$-alkoxy, $R^4$ is $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1H, 1-pyrazol-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl or piperidin-1-yl, or phenyl in each case substituted by s radicals from the group consisting of methyl, ethyl, methoxy, trifluoromethyl and halogen, $R^5$ is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, $R^6$ is halogen, cyano, nitro, $(C_1-C_6)$-alkyl, $(C_2-C_6)$-alkenyl, $(C_2-C_6)$-alkynyl, halo-$(C_1-C_6)$-alkyl, $(C_3-C_6)$-cycloalkyl, $(C_1-C_6)$-alkoxy, halo-$(C_1-C_6)$-alkoxy, $(C_1-C_6)$-alkylthio, $(C_1-C_6)$-alkylsulfinyl, $(C_1-C_6)$-alkylsulfonyl, phenyl, methylenedioxo, Y and Z are each independently O or S, $W^1$ is $(C_1-C_{10})$-alkylene, G is heteroaryl or heterocyclyl, each of which is substituted by s radicals from the group consisting of halogen, nitro, cyano, $(C_1-C_6)$-alkyl, halo-$(C_1-C_3)$-alkyl, cyclopropyl, $S(O)_n$—$(C_1-C_3)$-alkyl, $(C_1-C_4)$-alkoxy, halo-$(C_1-C_4)$-alkoxy and $(C_1-C_4)$-alkoxy-$(C_1-C_4)$-alkyl, where heterocyclyl bears n oxo groups, n is 0, 1 or 2, p is 0, 1, 2 or 3, s is 0, 1, 2, 3, 4 or 5.

In all the formulae specified hereinafter, the substituents and symbols, unless defined otherwise, are each as defined as in formula (I).

Inventive compounds can be prepared, for example, according to Scheme 1 by the methods specified in WO 2012/028579 A1. These methods include the reaction of an acid (III) with an amine Q-H and the reaction of an acyl chloride (II) with an amine Q-H.

Scheme 1

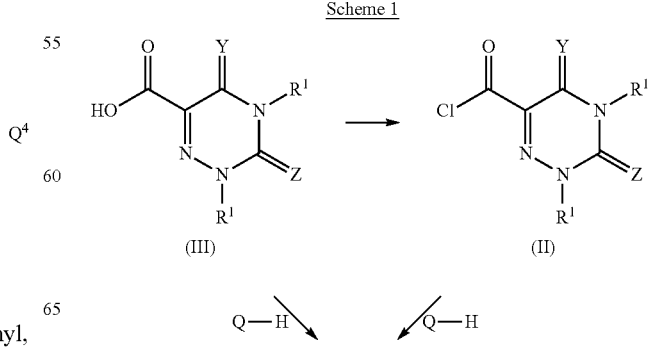

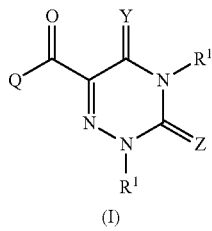

(I)

The requisite 1,2,4-triazine-3,5-dione-6-carbonyl chlorides (II) or their parent 1,2,4-triazine-3,5-dione-6-carboxylic acids (III) can be prepared, for example, by the methods described in WO2012/0020961.

It may be appropriate to alter the sequence of the reaction steps. For instance, benzoic acids bearing a sulfoxide cannot be converted directly to their acid chlorides. One option here is first to prepare the amide at the thioether stage and then to oxidize the thioether to the sulfoxide.

Libraries of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in Chem Files, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), referred to collectively as "inventive compounds" hereinafter, have excellent herbicidal efficacy against a broad spectrum of economically important monocotyledonous and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria,*

*Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage of the time of application, or they die completely after a certain time, such that competition by the weeds, which is harmful to the crop plants, is thus eliminated very early and in a lasting manner.

Although the inventive compounds have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular inventive compound and its application rate. For these reasons, the present compounds are very suitable for selective control of unwanted plant growth in plant crops such as agriculturally useful plants or ornamental plants.

In addition, the inventive compounds (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous plants since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, transgenic plants are notable for particular advantageous properties, for example for resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferable with regard to transgenic crops to use the inventive compounds in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables. The inventive compounds can preferably be used as herbicides in crops of useful plants which are resistant, or have been made resistant by recombinant means, to the phytotoxic effects of the herbicides.

Preference is given to the use of the inventive compounds or salts thereof in economically important transgenic crops of useful plants and ornamental plants, for example of cereals such as wheat, barley, rye, oats, millet, rice, cassava and corn, or else crops of sugar beet, cotton, soybean, oilseed rape, potatoes, tomatoes, peas and other vegetables. The inventive compounds can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806),
  transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659),
  transgenic crop plants, for example cotton, capable of producing *Bacillus thuringiensis* toxins (Bt toxins), which make the plants resistant to particular pests (EP 0142924 A, EP 0193259 A),
  transgenic crop plants with a modified fatty acid composition (WO 91/13972),
  genetically modified crop plants with novel constituents or secondary metabolites, for example novel phytoalexins, which bring about an increased disease resistance (EPA 309862, EPA0464461),
  genetically modified plants having reduced photorespiration, which have higher yields and higher stress tolerance (EPA 0305398),
  transgenic crop plants which produce pharmaceutically or diagnostically important proteins ("molecular pharming")
  transgenic crop plants which feature higher yields or better quality,
  transgenic crop plants which feature a combination, for example, of the abovementioned novel properties ("gene stacking")

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The inventive compounds can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the inventive active ingredients are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of harmful plants in transgenic crop plants.

The inventive compounds can be applied in the form of wettable powders, emulsifiable concentrates, sprayable solutions, dusting products or granules in the customary formulations. The invention therefore also provides herbicidal and plant-growth-regulating compositions which comprise the inventive compounds.

The inventive compounds can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986, Wade van Valkenburg, "Pesticide Formulations", Marcel Dekker, N.Y., 1973, K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyethoxylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylates or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of inventive compounds.

In wettable powders, the active ingredient concentration is, for example, about 10 to 90% by weight, the remainder to 100% by weight consisting of customary formulation constituents. In emulsifiable concentrates, the active ingredient concentration may be about 1 to 90% and preferably 5 to 80% by weight. Dustable formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active ingredient is present in liquid or solid form and on which granulation auxiliaries, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

1. Synthesis of 4-phenyl-2-methyl-N-(1-methyltetrazol-5-yl)-1,2,4-triazin-3,5-dione-6-carboxamide Table Example No. 1-12

To 185 mg (0.75 mmol) of 4-phenyl-2-methyl-1,2,4-triazine-3,5-dione-6-carboxylic acid and 113 mg (1.15 mmol) of 1-methyl-5-aminotetrazole in 2 ml of pyridine are added, at 0° C., 116 mg (0.98 mmol) of thionyl chloride. The mixture is stirred at room temperature (RT) for 16 h. Subsequently, 2N hydrochloric acid is added, and the product is filtered off with suction and washed with water. Yield 195 mg (79%).

The examples listed in the tables which follow are prepared analogously to the abovementioned methods or are obtainable analogously to the abovementioned methods. These compounds are very particularly preferred.

The abbreviations used mean:

| | | | |
|---|---|---|---|
| Et = ethyl | Me = methyl | nPr = n-propyl | cPr = cyclopropyl |
| Ph = phenyl | | | |

TABLE 1

Inventive compounds of the general formula (I) in which Q is $Q^1$, Y is oxygen, and $R^2$ is methyl.

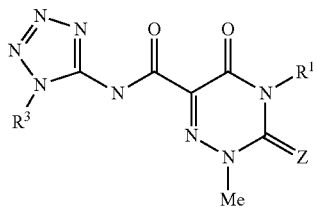

| No. | $R^3$ | $R^1$ | Z | Physical data ($^1$H NMR, DMSO-$d_6$, 400 MHz) |
|---|---|---|---|---|
| 1-1 | Me | Me | O | 11.32 (brs, 1H), 3.92 (s, 3H), 3.65 (s, 3H), 3.23 (s, 3H) |
| 1-2 | Et | Me | O | 4.27 (q, 2H), 3.65 (s, 3H), 3.22 (s, 3H), 1.43 (t, 3H) |
| 1-3 | nPr | Me | O | |
| 1-4 | Me | Et | O | |
| 1-5 | Et | Et | O | |
| 1-6 | Me | nPr | O | |
| 1-7 | Me | iPr | O | |
| 1-8 | Me | cPr | O | |
| 1-9 | Me | $C_2H_4$OMe | O | |
| 1-10 | Me | $C_2H_4$OEt | O | |
| 1-11 | Me | $CH_2$cPr | O | |
| 1-12 | Me | Ph | O | 11.33 (brs, 1H), 7.56-7.48 (m, 3H), 7.33 (d, 2H), 3.92 (s, 3H), 3.69 (s, 3H) |
| 1-13 | Me | Ph | S | |
| 1-14 | Et | Ph | O | 11.23 (brs, 1H), 7.56-7.48 (m, 3H), 7.33 (d, 2H), 4.27 (q, 2H), 3.69 (s, 3H), 1.42 (t, 3H) |
| 1-15 | Et | Ph | S | |
| 1-16 | nPr | Ph | O | |
| 1-17 | $C_2H_4$OMe | Ph | O | |
| 1-18 | Me | 2-MePh | O | |
| 1-19 | Me | 3-MePh | O | |
| 1-20 | Me | 4-MePh | O | |
| 1-21 | Me | 2-EtPh | O | |
| 1-22 | Me | 2-iPrPh | O | |
| 1-23 | Me | 2-cPrPh | O | |
| 1-24 | Me | 2-$CF_3$Ph | O | |
| 1-25 | Me | 3-$CF_3$Ph | O | |
| 1-26 | Me | 4-$CF_3$Ph | O | |
| 1-27 | Me | 2-CNPh | O | |
| 1-28 | Me | 2-$NO_2$Ph | O | |
| 1-29 | Me | 3-$NO_2$Ph | O | |
| 1-30 | Me | 4-$NO_2$Ph | O | |
| 1-31 | Me | 2-OMePh | O | |
| 1-32 | Me | 3-OMePh | O | |
| 1-33 | Me | 4-OMePh | O | |
| 1-34 | Me | 2-FPh | O | |
| 1-35 | Me | 3-FPh | O | |
| 1-36 | Me | 4-FPh | O | |
| 1-37 | Me | 2-ClPh | O | 11.45 (brs, 1H), 7.71-7.69 (m, 1H), 7.57-7.53 (m, 3H), 3.93 (s, 3H), 3.72 (s, 3H) |
| 1-38 | Me | 3-ClPh | O | |
| 1-39 | Me | 4-ClPh | O | |
| 1-40 | Me | 2,4-$Me_2$Ph | O | |
| 1-41 | Me | 2,4-$(MeO)_2$Ph | O | |
| 1-42 | Me | 3,4,5-$(MeO)_3$Ph | O | |
| 1-43 | Me | 2-OMe-5-Cl—Ph | O | 11.40 (brs, 1H), 7.53 (dd, 1H), 7.42 (d, 1H), 7.24 (d, 1H), 3.94 (s, 3H), 3.79 (s, 3H), 3.72 (s, 3H) |
| 1-44 | Me | 3,4-$(OCH_2O)$Ph | O | 11.31 (brs, 1H), 7.05 (d, 1H), 6.89 (d, 1H), 6.80 (dd, 1H), 6.12 (s, 2H), 3.92 (s, 3H), 3.68 (s, 3H) |

TABLE 2

Inventive compounds of the general formula (I) in which Q is $Q^2$, Y is oxygen, and $R^2$ is methyl.

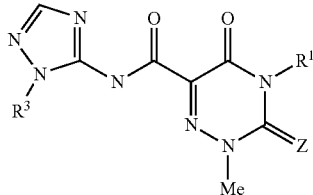

| No. | $R^3$ | $R^1$ | Z | Physical data ($^1$H NMR, DMSO-$d_6$, 400 MHz) |
|---|---|---|---|---|
| 2-1 | Me | Me | O | 7.91 (s, 1H), 3.69 (s, 3H), 3.64 (s, 3H), 3.22 (s, 3H) |
| 2-2 | Me | Et | O | |
| 2-3 | Me | nPr | O | |
| 2-4 | Me | iPr | O | |
| 2-5 | Me | cPr | O | |
| 2-6 | Me | C$_2$H$_4$OMe | O | |
| 2-7 | Me | C$_2$H$_4$OEt | O | |
| 2-8 | Me | CH$_2$cPr | O | |
| 2-9 | Me | Ph | O | 7.91 (s, 1H), 7.55-7.48 (m, 3H), 7.33 (d, 2H), 3.69 (s, 3H), 3.67 (s, 3H) |
| 2-10 | Me | Ph | S | |
| 2-11 | Me | 2-MePh | O | |
| 2-12 | Me | 3-MePh | O | |
| 2-13 | Me | 4-MePh | O | |
| 2-14 | Me | 2-EtPh | O | |
| 2-15 | Me | 2-iPrPh | O | |
| 2-16 | Me | 2-cPrPh | O | |
| 2-17 | Me | 2-CF$_3$Ph | O | |
| 2-18 | Me | 3-CF$_3$Ph | O | |
| 2-19 | Me | 4-CF$_3$Ph | O | |
| 2-20 | Me | 2-CNPh | O | |
| 2-21 | Me | 2-NO$_2$Ph | O | |
| 2-22 | Me | 3-NO$_2$Ph | O | |
| 2-23 | Me | 4-NO$_2$Ph | O | |
| 2-24 | Me | 2-OMePh | O | |
| 2-25 | Me | 3-OMePh | O | |
| 2-26 | Me | 4-OMePh | O | |
| 2-27 | Me | 2-FPh | O | |
| 2-28 | Me | 3-FPh | O | |
| 2-29 | Me | 4-FPh | O | |
| 2-30 | Me | 2-ClPh | O | |
| 2-31 | Me | 3-ClPh | O | |
| 2-32 | Me | 4-ClPh | O | |
| 2-33 | Me | 2,4-Me$_2$Ph | O | |
| 2-34 | Me | 2,4-(MeO)$_2$Ph | O | |
| 2-35 | Me | 3,4,5-(MeO)$_3$Ph | O | |
| 2-36 | Me | 2-OMe-5-Cl—Ph | O | |
| 2-37 | Me | 3,4-(OCH$_2$O)Ph | O | |

TABLE 3

Inventive compounds of the general formula (I) in which Q is $Q^3$, Y is oxygen, and $R^2$ is methyl.

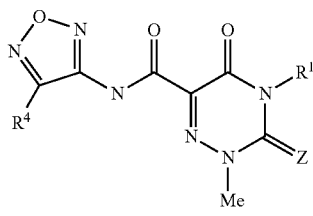

| No. | $R^4$ | $R^1$ | Z | Physical data ($^1$H NMR, DMSO-$d_6$, 400 MHz) |
|---|---|---|---|---|
| 3-1 | Me | Me | O | 11.21 (brs, 1H), 3.65 (s, 3H), 3.23 (s, 3H), 2.35 (s, 3H) |
| 3-2 | Me | Et | O | |
| 3-3 | Me | nPr | O | |
| 3-4 | Me | iPr | O | |
| 3-5 | Me | cPr | O | |
| 3-6 | Me | C$_2$H$_4$OMe | O | |
| 3-7 | Me | C$_2$H$_4$OEt | O | |
| 3-8 | Me | CH$_2$cPr | O | |
| 3-9 | Me | Ph | O | 11.17 (brs, 1H), 7.57-7.49 (m, 3H), 7.34 m, 2H), 3.69 (s, 3H), 2.33 (s, 3H) |
| 3-10 | Me | Ph | S | |
| 3-11 | Me | 2-MePh | O | |
| 3-12 | Me | 3-MePh | O | |
| 3-13 | Me | 4-MePh | O | |
| 3-14 | Me | 2-EtPh | O | |
| 3-15 | Me | 2-iPrPh | O | |
| 3-16 | Me | 2-cPrPh | O | |
| 3-17 | Me | 2-CF$_3$Ph | O | |
| 3-18 | Me | 3-CF$_3$Ph | O | |
| 3-19 | Me | 4-CF$_3$Ph | O | |
| 3-20 | Me | 2-CNPh | O | |
| 3-21 | Me | 2-NO$_2$Ph | O | |
| 3-22 | Me | 3-NO$_2$Ph | O | |
| 3-23 | Me | 4-NO$_2$Ph | O | |
| 3-24 | Me | 2-OMePh | O | |
| 3-25 | Me | 3-OMePh | O | |
| 3-26 | Me | 4-OMePh | O | |
| 3-27 | Me | 2-FPh | O | |
| 3-28 | Me | 3-FPh | O | |
| 3-29 | Me | 4-FPh | O | |
| 3-30 | Me | 2-ClPh | O | |
| 3-31 | Me | 3-ClPh | O | |
| 3-32 | Me | 4-ClPh | O | |
| 3-33 | Me | 2,4-Me$_2$Ph | O | |
| 3-34 | Me | 2,4-(MeO)$_2$Ph | O | |
| 3-35 | Me | 3,4,5-(MeO)$_3$Ph | O | |
| 3-36 | Me | 2-OMe-5-Cl—Ph | O | |
| 3-37 | Me | 3,4-(OCH$_2$O)Ph | O | |
| 3-38 | Cl | Me | O | |
| 3-39 | Cl | Et | O | |
| 3-40 | Cl | nPr | O | |
| 3-41 | Cl | iPr | O | |
| 3-42 | Cl | cPr | O | |
| 3-43 | Cl | C$_2$H$_4$OMe | O | |
| 3-44 | Cl | C$_2$H$_4$OEt | O | |
| 3-45 | Cl | CH$_2$cPr | O | |
| 3-46 | Cl | Ph | O | |
| 3-47 | Cl | Ph | S | |
| 3-48 | Cl | 2-MePh | O | |
| 3-49 | Cl | 3-MePh | O | |
| 3-50 | Cl | 4-MePh | O | |
| 3-51 | Cl | 2-EtPh | O | |
| 3-52 | Cl | 2-iPrPh | O | |
| 3-53 | Cl | 2-cPrPh | O | |
| 3-54 | Cl | 2-CF$_3$Ph | O | |
| 3-55 | Cl | 3-CF$_3$Ph | O | |
| 3-56 | Cl | 4-CF$_3$Ph | O | |
| 3-57 | Cl | 2-CNPh | O | |
| 3-58 | Cl | 2-NO$_2$Ph | O | |
| 3-59 | Cl | 3-NO$_2$Ph | O | |
| 3-60 | Cl | 4-NO$_2$Ph | O | |
| 3-61 | Cl | 2-OMePh | O | |
| 3-62 | Cl | 3-OMePh | O | |
| 3-63 | Cl | 4-OMePh | O | |

TABLE 3-continued

Inventive compounds of the general formula (I) in which Q is $Q^3$, Y is oxygen, and $R^2$ is methyl.

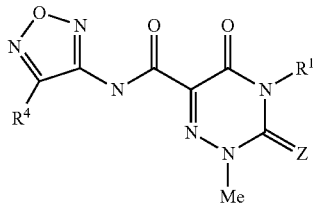

| No. | $R^4$ | $R^1$ | Z | Physical data ($^1$H NMR, DMSO-$d_6$, 400 MHz) |
|---|---|---|---|---|
| 3-64 | Cl | 2-FPh | O | |
| 3-65 | Cl | 3-FPh | O | |
| 3-66 | Cl | 4-FPh | O | |
| 3-67 | Cl | 2-ClPh | O | |
| 3-68 | Cl | 3-ClPh | O | |
| 3-69 | Cl | 4-ClPh | O | |
| 3-70 | Cl | 2,4-Me$_2$Ph | O | |
| 3-71 | Cl | 2,4-(MeO)$_2$Ph | O | |
| 3-72 | Cl | 3,4,5-(MeO)$_3$Ph | O | |
| 3-73 | Cl | 2-OMe-5-Cl—Ph | O | |
| 3-74 | Cl | 3,4-(OCH$_2$O)Ph | O | |

TABLE 4

Inventive compounds of the general formula (I) in which Q is $Q^4$, Y is oxygen, and $R^2$ is methyl.

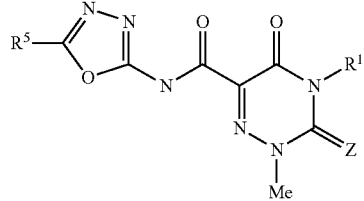

| No. | $R^5$ | $R^1$ | Z | Physical data ($^1$H NMR, DMSO-$d_6$, 400 MHz) |
|---|---|---|---|---|
| 4-1 | Me | Me | O | |
| 4-2 | Me | Et | O | |
| 4-3 | Me | nPr | O | |
| 4-4 | Me | iPr | O | |
| 4-5 | Me | cPr | O | |
| 4-6 | Me | C$_2$H$_4$OMe | O | |
| 4-7 | Me | C$_2$H$_4$OEt | O | |
| 4-8 | Me | CH$_2$cPr | O | |
| 4-9 | Me | Ph | O | 7.55-7.48 (m, 3H), 7.32 (d, 2H), 3.66 (s, 3H) ), 2.47 (s, 3H) |
| 4-10 | Me | Ph | S | |
| 4-11 | Me | 2-MePh | O | |
| 4-12 | Me | 3-MePh | O | |
| 4-13 | Me | 4-MePh | O | |
| 4-14 | Me | 2-EtPh | O | |
| 4-15 | Me | 2-iPrPh | O | |
| 4-16 | Me | 2-cPrPh | O | |
| 4-17 | Me | 2-CF$_3$Ph | O | |
| 4-18 | Me | 3-CF$_3$Ph | O | |
| 4-19 | Me | 4-CF$_3$Ph | O | |
| 4-20 | Me | 2-CNPh | O | |
| 4-21 | Me | 2-NO$_2$Ph | O | |
| 4-22 | Me | 3-NO$_2$Ph | O | |
| 4-23 | Me | 4-NO$_2$Ph | O | |
| 4-24 | Me | 2-OMePh | O | |
| 4-25 | Me | 3-OMePh | O | |
| 4-26 | Me | 4-OMePh | O | |
| 4-27 | Me | 2-FPh | O | |

TABLE 4-continued

Inventive compounds of the general formula (I) in which Q is $Q^4$, Y is oxygen, and $R^2$ is methyl.

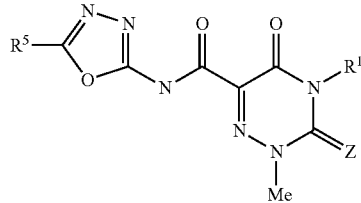

| No. | $R^5$ | $R^1$ | Z | Physical data ($^1$H NMR, DMSO-$d_6$, 400 MHz) |
|---|---|---|---|---|
| 4-28 | Me | 3-FPh | O | |
| 4-29 | Me | 4-FPh | O | |
| 4-30 | Me | 2-ClPh | O | |
| 4-31 | Me | 3-ClPh | O | |
| 4-32 | Me | 4-ClPh | O | |
| 4-33 | Me | 2,4-Me$_2$Ph | O | |
| 4-34 | Me | 2,4-(MeO)$_2$Ph | O | |
| 4-35 | Me | 3,4,5-(MeO)$_3$Ph | O | |
| 4-36 | Me | 2-OMe-5-Cl—Ph | O | |
| 4-37 | Me | 3,4-(OCH$_2$O)Ph | O | |
| 4-38 | Et | Me | O | |
| 4-39 | Et | Et | O | |
| 4-40 | Et | nPr | O | |
| 4-41 | Et | iPr | O | |
| 4-42 | Et | cPr | O | |
| 4-43 | Et | C$_2$H$_4$OMe | O | |
| 4-44 | Et | C$_2$H$_4$OEt | O | |
| 4-45 | Et | CH$_2$cPr | O | |
| 4-46 | Et | Ph | O | |
| 4-47 | Et | Ph | S | |
| 4-48 | Et | 2-MePh | O | |
| 4-49 | Et | 3-MePh | O | |
| 4-50 | Et | 4-MePh | O | |
| 4-51 | Et | 2-EtPh | O | |
| 4-52 | Et | 2-iPrPh | O | |
| 4-53 | Et | 2-cPrPh | O | |
| 4-54 | Et | 2-CF$_3$Ph | O | |
| 4-55 | Et | 3-CF$_3$Ph | O | |
| 4-56 | Et | 4-CF$_3$Ph | O | |
| 4-57 | Et | 2-CNPh | O | |
| 4-58 | Et | 2-NO$_2$Ph | O | |
| 4-59 | Et | 3-NO$_2$Ph | O | |
| 4-60 | Et | 4-NO$_2$Ph | O | |
| 4-61 | Et | 2-OMePh | O | |
| 4-62 | Et | 3-OMePh | O | |
| 4-63 | Et | 4-OMePh | O | |
| 4-64 | Et | 2-FPh | O | |
| 4-65 | Et | 3-FPh | O | |
| 4-66 | Et | 4-FPh | O | |
| 4-67 | Et | 2-ClPh | O | |
| 4-68 | Et | 3-ClPh | O | |
| 4-69 | Et | 4-ClPh | O | |
| 4-70 | Et | 2,4-Me$_2$Ph | O | |
| 4-71 | Et | 2,4-(MeO)$_2$Ph | O | |
| 4-72 | Et | 3,4,5-(MeO)$_3$Ph | O | |
| 4-73 | Et | 2-OMe-5-Cl—Ph | O | |
| 4-74 | Et | 3,4-(OCH$_2$O)Ph | O | |
| 4-75 | OCH$_2$Me | Me | O | |
| 4-76 | OCH$_2$Me | Et | O | |
| 4-77 | OCH$_2$Me | nPr | O | |
| 4-78 | OCH$_2$Me | iPr | O | |
| 4-79 | OCH$_2$Me | cPr | O | |
| 4-80 | OCH$_2$Me | C$_2$H$_4$OMe | O | |
| 4-81 | OCH$_2$Me | C$_2$H$_4$OEt | O | |
| 4-82 | OCH$_2$Me | CH$_2$cPr | O | |
| 4-83 | OCH$_2$Me | Ph | O | |
| 4-84 | OCH$_2$Me | Ph | S | |
| 4-85 | OCH$_2$Me | 2-MePh | O | |
| 4-86 | OCH$_2$Me | 3-MePh | O | |
| 4-87 | OCH$_2$Me | 4-MePh | O | |
| 4-88 | OCH$_2$Me | 2-EtPh | O | |
| 4-89 | OCH$_2$Me | 2-iPrPh | O | |

TABLE 4-continued

Inventive compounds of the general formula (I) in which Q is $Q^4$, Y is oxygen, and $R^2$ is methyl.

| No. | $R^5$ | $R^1$ | Z | Physical data ($^1$H NMR, DMSO-$d_6$, 400 MHz) |
|---|---|---|---|---|
| 4-90 | OCH$_2$Me | 2-cPrPh | O | |
| 4-91 | OCH$_2$Me | 2-CF$_3$Ph | O | |
| 4-92 | OCH$_2$Me | 3-CF$_3$Ph | O | |
| 4-93 | OCH$_2$Me | 4-CF$_3$Ph | O | |
| 4-94 | OCH$_2$Me | 2-CNPh | O | |
| 4-95 | OCH$_2$Me | 2-NO$_2$Ph | O | |
| 4-96 | OCH$_2$Me | 3-NO$_2$Ph | O | |
| 4-97 | OCH$_2$Me | 4-NO$_2$Ph | O | |
| 4-98 | OCH$_2$Me | 2-OMePh | O | |
| 4-99 | OCH$_2$Me | 3-OMePh | O | |
| 4-100 | OCH$_2$Me | 4-OMePh | O | |
| 4-101 | OCH$_2$Me | 2-FPh | O | |
| 4-102 | OCH$_2$Me | 3-FPh | O | |
| 4-103 | OCH$_2$Me | 4-FPh | O | |
| 4-104 | OCH$_2$Me | 2-ClPh | O | |
| 4-105 | OCH$_2$Me | 3-ClPh | O | |
| 4-106 | OCH$_2$Me | 4-ClPh | O | |
| 4-107 | OCH$_2$Me | 2,4-Me$_2$Ph | O | |
| 4-108 | OCH$_2$Me | 2,4-(MeO)$_2$Ph | O | |
| 4-109 | OCH$_2$Me | 3,4,5-(MeO)$_3$Ph | O | |
| 4-110 | OCH$_2$Me | 2-OMe-5-Cl—Ph | O | |
| 4-111 | OCH$_2$Me | 3,4-(OCH$_2$O)Ph | O | |

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
75 parts by weight of a compound of the formula (I) and/or salts thereof,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting, in a colloid mill,
25 parts by weight of a compound of the formula (I) and/or salts thereof,
5 parts by weight of sodium 2,2'-dinaphthylmethane-6,6'-disulfonate,
2 parts by weight of sodium oleoylmethyltaurate,
1 part of polyvinyl alcohol,
17 parts by weight of calcium carbonate and
50 parts by weight of water,
then grinding the mixture in a bead mill and atomizing and drying the suspension thus obtained in a spray tower by means of a one-phase nozzle.

C. BIOLOGICAL EXAMPLES

1. Pre-Emergence Herbicidal Action Against Harmful Plants

Seeds of monocotyledonous and dicotyledonous weed plants and crop plants are laid out in wood fiber pots in sandy loam and covered with soil. The inventive compounds, formulated in the form of wettable powders (WP) or as emulsion concentrates (EC), are then applied to the surface of the soil cover in the form of an aqueous suspension or emulsion at a water application rate equating to 600 to 800 l/ha, with addition of 0.2% wetting agent. After the treatment, the pots are placed in a greenhouse and kept under good growth conditions for the test plants. The damage to the trial plants is scored visually after a test period of 3 weeks by comparison with untreated controls (herbicidal efficacy in percent (%): 100% efficacy=the plants have died, 0% efficacy=like control plants). In this test, for example, compounds no. 1-1 and 1-12 at an application rate of 320 g/ha show at least 80% efficacy against *Avena fatua, Cyperus serotinus, Echinochloa crus galli, Abutilon theophrasti, Amaranthus retroflexus, Stellaria media* and *Viola tricolor.*

2. Post-Emergence Herbicidal Action Against Harmful Plants

Seeds of monocotyledonous and dicotyledonous weed plants and crop plants are laid out in wood fiber pots in sandy loam, covered with soil and cultivated in a greenhouse under good growth conditions. 2 to 3 weeks after sowing, the test plants are treated at the one-leaf stage. The inventive compounds, formulated in the form of wettable powders (WP) or as emulsion concentrates (EC), are then applied to the green parts of the plants in the form of an aqueous suspension or emulsion at a water application rate equating to 600 to 800 l/ha, with addition of 0.2% wetting agent. After the trial plants have been left to stand in a greenhouse under optimal growth conditions for about 3 weeks, the efficacy of the formulations is scored visually in comparison to untreated controls (herbicidal efficacy in percent (%): 100% efficacy=the plants have died, 0% efficacy=like control plants). In this test, for example, compounds no. 1-1 and 1-12 at an application rate of 80 g/ha show at least 80% efficacy against *Echinochloa crus galli, Abutilon theophrasti, Amaranthus retroflexus* and *Veronica persica.*

The invention claimed is:
1. 1,2,4-Triazine-3,5-dione-6-carboxamide of formula (I) or salt thereof

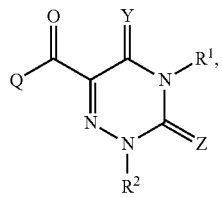

(I)

in which the substituents are defined as follows:

$R^1$ is $(C_1-C_{10})$-alkyl, $(C_2-C_{10})$-alkenyl, $(C_2-C_{10})$-alkynyl, halo-$(C_1-C_{10})$-alkyl, halo-$(C_2-C_{10})$-alkenyl, halo-$(C_2-C_{10})$-alkynyl, $(C_3-C_{10})$-cycloalkyl, halo-$(C_3-C_{10})$-cycloalkyl, $(C_1-C_4)$-alkyl-$(C_3-C_7)$-cycloalkyl, $(C_3-C_7)$-cycloalkyl-$(C_1-C_6)$-alkyl, $(C_3-C_7)$-cycloalkyl-$(C_3-C_7)$-cycloalkyl, halo-$(C_3-C_7)$-cycloalkyl-$(C_1-C_6)$-alkyl, $(C_1-C_6)$-alkyl-$(C_3-C_7)$-cycloalkyl-$(C_1-C_6)$-alkyl, $(C_3-C_{12})$-cycloalkenyl, halo-$(C_3-C_{12})$-cycloalkenyl, $(C_1-C_6)$-alkoxy-$(C_1-C_6)$-alkyl, $(C_1-C_6)$-alkoxy-$(C_2-C_6)$-alkenyl, $(C_1-C_6)$-alkyl-$(C_3-C_7)$-cycloalkyl, $(C_1-C_6)$-alkoxy-$(C_3-C_7)$-cycloalkyl, $(C_3-C_7)$-cycloalkoxy-$(C_1-C_6)$-alkyl, $(C_3-C_7)$-cycloalkoxy-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkylamino-$(C_1-C_6)$-alkyl, di-$(C_1-C_6)$-alkylamino-$(C_1-C_6)$-alkyl, halo-$(C_1-C_6)$-alkylamino-$(C_1-C_6)$-alkyl, $(C_3-C_7)$-cycloalkylamino-$(C_1-C_6)$-alkyl, $(C_1-C_6)$-alkylcarbonyl, halo-$(C_1-C_6)$-alkylcarbonyl, $(C_3-C_7)$-cycloalkylcarbonyl, $(C_1-C_6)$-alkoxycarbonyl, $(C_3-C_7)$-cycloalkoxycarbonyl, $(C_3-C_7)$-cycloalkyl-$(C_1-C_6)$-alkoxycarbonyl, $(C_1-C_6)$-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxyhalo-$(C_1-C_6)$-alkyl, halo-$(C_1-C_6)$-alkoxyhalo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10})$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-C_6)$-alkylamino, halo-$(C_1-C_6)$-alkylamino, halodi-$(C_1-C_6)$-alkylamino, $(C_3-C_{12})$-cycloalkylamino, $(C_1-C_6)$-alkylcarbonylamino, halo-$(C_1-C_6)$-alkylcarbonylamino, $(C_1-C_{10})$-alkylsulfonylamino, halo-$(C_1-C_{10})$-alkylsulfonylamino, $(C_3-C_7)$-cycloalkyl-$(C_1-C_6)$-alkylamino, cyano, hydroxyl, amino, C(=O)OH, C(=O)NHOH, $SO_2NH_2$, $SO_2NHCN$, $SO_2NHOH$, NHCHO, or $R^1$ is phenyl, phenylsulfonyl, $W^1$-(phenyl), $W^1$—(O-phenyl), $W^1$—(S-phenyl), $W^1$—($SO_2$-phenyl), $W^2$—($SO_2CH_2$-phenyl) or $W^2$—($SCH_2$-phenyl), where the phenyl rings of the seven aforementioned radicals each bear s $R^6$ substituents, or $R^1$ is G, $W^2G$ or $W^2OG$, $R^2$ is hydrogen, $(C_1-C_4)$-alkyl, $(C_1-C_4)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, where the phenyl or heteroaryl rings of the four aforementioned radicals each bear s $R^6$ substituents, Q is a $Q^1$, $Q^2$, $Q^3$ or $Q^4$ radical,

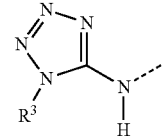

$Q^1$

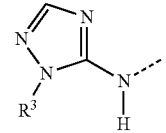

$Q^2$

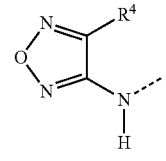

$Q^3$

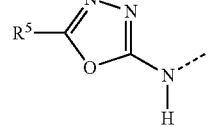

$Q^4$ $R^3$ is $(C_1-C_8)$-alkyl, $(C_2-C_8)$-alkenyl, $(C_2-C_8)$-alkynyl, where these radicals are each substituted by s radicals from the group consisting of halogen, cyano, hydroxyl, nitro, $SiR^{10}{}_3$, $PO(OR^{10})_2$, $S(O)_n$—$(C_1-C_6)$-alkyl, $(C_1-C_6)$-alkoxy, halo-$(C_1-C_6)$-alkoxy, $COR^{3a}$, $COOR^{3a}$, $OCOR^{3a}$, $NR^{3a}COR^{3a}$, $NR^{3a}SO_2R^{3b}$, $(C_3-C_6)$-cycloalkyl, heteroaryl, heterocyclyl or phenyl, where the 4 latter radicals are each substituted by p radicals from the group consisting of methyl, ethyl, methoxy, trifluoromethyl, cyano and halogen, and where heterocyclyl bears n oxo groups, or $R^3$ is phenyl substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{3a}$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{3b}$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, $(C_1-C_6)$-alkoxy-$(C_1-C_6)$-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by p radicals from the group consisting of methyl, ethyl, methoxy, trifluoromethyl and halogen, $R^5$ is hydrogen, $(C_1-C_6)$-alkyl, $(C_1-C_6)$-alkoxy-$(C_1-C_6)$-alkyl, $CH_2R^{5a}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^6$, $NHR^6$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl or methylsulfonyl, or heteroaryl, heterocyclyl, benzyl or phenyl, each of which is substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{5a}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy or $(C_3-C_6)$-cycloalkyl, or heteroaryl or heterocyclyl, each of which is substituted by p radicals from the group consisting of methyl, ethyl, methoxy, trifluoromethyl and halogen, Y and Z are each independently O or S, $W^1$ is $(C_1-C_{10})$-alkylene, $(C_2-C_6)$-alkenylene or $(C_2-C_6)$-alkynylene, $W^2$ is $(C_1-C_{10})$-alkylene, G is heteroaryl or heterocyclyl, each of which is substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, where heterocyclyl bears n oxo groups, $R^6$ is halogen, cyano, hydroxyl, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —OCN, —SCN, —SF$_5$, $(C_1-C_6)$-alkyl, $(C_2-C_6)$-alkenyl, $(C_2-C_6)$-alkynyl, halo-$(C_1-C_6)$-alkyl, halo-$(C_2-C_6)$-alkenyl, halo-$(C_2-C_6)$-alkynyl, $(C_3-C_8)$-cycloalkyl, halo-$(C_3-C_8)$-cycloalkyl, $(C_1-C_6)$-alkyl-$(C_3-C_7)$-cycloalkyl, $(C_3-C_7)$-cycloalkyl-$(C_1-C_6)$-alkyl, $(C_3-C_8)$-cycloalkenyl, halo-$(C_3-C_8)$-cycloalkenyl, $(C_1-C_6)$-alkoxy-$(C_1-C_6)$-alkyl, $(C_3-C_7)$-cycloalkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_8)$-alkylsulfinyl-$(C_1-C_6)$-alkyl, $(C_1-C_6)$-alkoxyhalo-$(C_1-C_6)$-alkyl, cyano-$(C_1-C_6)$-alkyl, hydroxy-$(C_1-C_6)$-alkyl, $(C_1-C_6)$-alkoxy, halo-$(C_1-C_6)$-alkoxy, $(C_3-C_8)$-cycloalkoxy, halo-$(C_3-C_8)$-cycloalkoxy, $(C_3-C_8)$-cycloalkyl-$(C_1-C_6)$-alkoxy, $(C_2-C_6)$-alkenyloxy, halo-$(C_2-C_6)$-alkenyloxy, $(C_1-C_6)$-alkoxy-$(C_1-C_6)$-alkoxy, $(C_2-C_6)$-alkylcarbonyloxy, $(C_1-C_6)$-alkylthio, halo-$(C_1-C_6)$-alkylthio, $(C_3-C_8)$-cycloalkylthio, $(C_1-C_6)$-alkylsulfinyl, halo-$(C_1-C_6)$-alkylsulfinyl, $(C_1-C_6)$-alkylsulfonyl, halo-$(C_1-C_6)$-alkylsulfonyl, $(C_3-C_8)$-cycloalkylsulfonyl, $(C_1-C_6)$-alkylamino, di-$(C_1-C_6)$-alkylamino, halo-$(C_1-C_6)$-alkylamino, halodi-$(C_1-C_8)$-alkylamino or $(C_3-C_8)$-cycloalkylamino, or two vicinal $R^6$ radicals form a $(C_3-C_6)$-alkylene group in which p carbon atoms are replaced by oxygen, sulfur or nitrogen, and in which one carbon atom bears t oxo groups, n is 0, 1 or 2, p is 0, 1, 2 or 3, s is 0, 1, 2, 3, 4 or 5, t is 0 or 1.

2. 1,2,4-Triazine-3,5-dione-6-carboxamide of formula (I) or salt thereof as claimed in claim 1, in which $R^1$ is $(C_1-C_{10})$-alkyl, $(C_2-C_{10})$-alkenyl, $(C_2-C_{10})$-alkynyl, halo-$(C_1-C_{10})$-alkyl, halo-$(C_2-C_{10})$-alkenyl, halo-$(C_2-C_{10})$-alkynyl, $(C_3-C_{10})$-cycloalkyl, halo-$(C_3-C_{10})$-cycloalkyl, $(C_1-C_4)$-alkyl-$(C_3-C_7)$-cycloalkyl, $(C_3-C_7)$-cycloalkyl-$(C_1-C_6)$-alkyl, $(C_3-C_7)$-cycloalkyl-$(C_3-C_7)$-cycloalkyl, halo-$(C_3-C_7)$-cycloalkyl-$(C_1-C_6)$-alkyl, $(C_1-C_6)$-alkyl-$(C_3-C_7)$-cycloalkyl-$(C_1-C_6)$-alkyl, $(C_3-C_{12})$-cycloalkenyl, halo-$(C_3-C_{12})$-cycloalkenyl, $(C_1-C_6)$-alkoxy-$(C_1-C_6)$-alkyl, $(C_1-C_6)$-alkoxy-$(C_2-C_6)$-alkenyl, $(C_1-C_6)$-alkyl-$(C_3-C_7)$-cycloalkyl, $(C_1-C_6)$-alkoxy-$(C_3-C_7)$-cycloalkyl, $(C_3-C_7)$-cycloalkoxy-$(C_1-C_6)$-alkyl, $(C_3-C_7)$-cycloalkoxy-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkylamino-$(C_1-C_6)$-alkyl, di-$(C_1-C_6)$-alkylamino-$(C_1-C_6)$-alkyl, halo-$(C_1-C_6)$-alkylamino-$(C_1-C_6)$-alkyl, $(C_3-C_7)$-cycloalkylamino-$(C_1-C_6)$-alkyl, $(C_1-C_6)$-alkylcarbonyl, halo-$(C_1-C_6)$-alkylcarbonyl, $(C_3-C_7)$-cycloalkylcarbonyl, $(C_1-C_6)$-alkoxycarbonyl, $(C_3-C_7)$-cycloalkoxycarbonyl, $(C_3-C_7)$-cycloalkyl-$(C_1-C_6)$-alkoxycarbonyl, $(C_1-C_6)$-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxyhalo-$(C_1-C_6)$-alkyl, halo-$(C_1-C_6)$-alkoxyhalo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10})$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-

$C_6$)-alkylamino, halo-($C_1$-$C_6$)-alkylamino, halodi-($C_1$-$C_6$)-alkylamino, ($C_3$-$C_{12}$)-cycloalkylamino, ($C_1$-$C_6$)-alkylcarbonylamino, halo-($C_1$-$C_6$)-alkylcarbonylamino, ($C_1$-$C_{10}$)-alkylsulfonylamino, halo-($C_1$-$C_{10}$)-alkylsulfonylamino, ($C_3$-$C_7$)-cycloalkyl-($C_1$-$C_6$)-alkylamino, cyano, hydroxyl, amino, C(=O)OH, C(=O)NHOH, $SO_2NH_2$, $SO_2NHCN$, $SO_2NHOH$, NHCHO, or $R^1$ is phenyl, phenylsulfonyl, $W^1$-(phenyl), $W^1$—(O-phenyl), $W^1$—(S-phenyl), $W^1$—($SO_2$-phenyl), $W^2$—($SO_2CH_2$-phenyl) or $W^2$—($SCH_2$-phenyl), where the phenyl rings of the seven aforementioned radicals each bear s $R^6$ substituents, or $R^1$ is G or $W^2$G, $R^2$ is hydrogen, ($C_1$-$C_4$)-alkyl, ($C_1$-$C_4$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, where the phenyl or hetaryl rings of the four aforementioned radicals each bear s $R^6$ substituents, in which Q is a $Q^1$, $Q^2$, $Q^3$ or $Q^4$ radical,

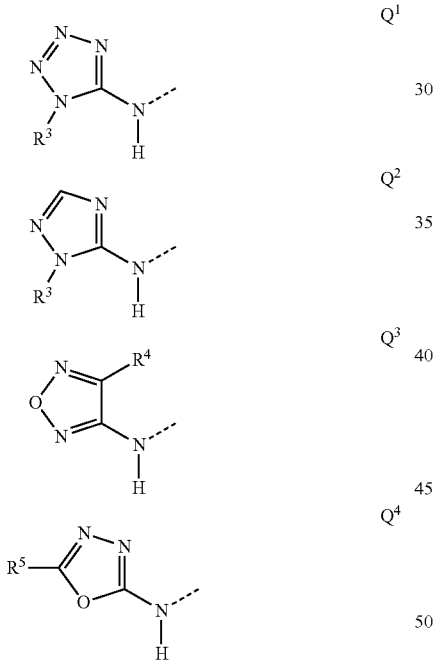

$R^3$ is ($C_1$-$C_8$)-alkyl, ($C_2$-$C_8$)-alkenyl, ($C_2$-$C_8$)-alkynyl, where these radicals are each substituted by s radicals from the group consisting of halogen, cyano, nitro, S(O)$_n$—($C_1$-$C_6$)-alkyl, ($C_1$-$C_6$)-alkoxy, halo-($C_1$-$C_6$)-alkoxy, ($C_3$-$C_6$)-cycloalkyl, heteroaryl, heterocyclyl or phenyl, where the 4 latter radicals are each substituted by p radicals from the group consisting of methyl, ethyl, methoxy, trifluoromethyl, cyano and halogen, and where heterocyclyl bears n oxo groups, or $R^3$ is phenyl substituted in each case by p radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, $R^4$ is ($C_1$-$C_6$)-alkyl, ($C_3$-$C_7$)-cycloalkyl, halo-($C_1$-$C_6$)-alkyl, ($C_1$-$C_6$)-alkoxy, halo-($C_1$-$C_6$)-alkoxy, cyano, nitro, methylsulfenyl, methylsulfinyl, methylsulfonyl, ($C_1$-$C_4$)-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl or piperidin-1-yl, or phenyl in each case substituted by p radicals from the group consisting of methyl, ethyl, methoxy, trifluoromethyl and halogen, $R^5$ is hydrogen, ($C_1$-$C_6$)-alkyl, ($C_3$-$C_7$)-cycloalkyl, halo-($C_1$-$C_6$)-alkyl, ($C_3$-$C_7$)-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, $R^6$ is halogen, cyano, hydroxyl, amino, nitro, —CHO, —C(=O)OH, —C(=O)$NH_2$, —C(=S)$NH_2$, —C(=O)NHCN, —C(=O)NHOH, —SH, —$SO_2NH_2$, —$SO_2NHCN$, —$SO_2NHOH$, —OCN, —SCN, —$SF_5$, ($C_1$-$C_6$)-alkyl, ($C_2$-$C_6$)-alkenyl, ($C_2$-$C_6$)-alkynyl, halo-($C_1$-$C_6$)-alkyl, halo-($C_2$-$C_6$)-alkenyl, halo-($C_2$-$C_6$)-alkynyl, ($C_3$-$C_8$)-cycloalkyl, halo-($C_3$-$C_8$)-cycloalkyl, ($C_1$-$C_6$)-alkyl-($C_3$-$C_7$)-cycloalkyl, ($C_3$-$C_7$)-cycloalkyl-($C_1$-$C_6$)-alkyl, ($C_3$-$C_8$)-cycloalkenyl, halo-($C_3$-$C_8$)-cycloalkenyl, ($C_1$-$C_6$)-alkoxy-($C_1$-$C_6$)-alkyl, ($C_3$-$C_7$)-cycloalkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkylthio-($C_1$-$C_6$)-alkyl, ($C_1$-$C_8$)-alkylsulfinyl-($C_1$-$C_6$)-alkyl, ($C_1$-$C_8$)-alkoxyhalo-($C_1$-$C_6$)-alkyl, cyano-($C_1$-$C_6$)-alkyl, hydroxy-($C_1$-$C_6$)-alkyl, ($C_1$-$C_6$)-alkoxy, halo-($C_1$-$C_6$)-alkoxy, ($C_3$-$C_8$)-cycloalkoxy, halo-($C_3$-$C_8$)-cycloalkoxy, ($C_3$-$C_8$)-cycloalkyl-($C_1$-$C_6$)-alkoxy, ($C_2$-$C_6$)-alkenyloxy, halo-($C_2$-$C_6$)-alkenyloxy, ($C_1$-$C_6$)-alkoxy-($C_1$-$C_6$)-alkoxy, ($C_2$-$C_6$)-alkylcarbonyloxy, ($C_1$-$C_6$)-alkylthio, halo-($C_1$-$C_6$)-alkylthio, ($C_3$-$C_8$)-cycloalkylthio, ($C_1$-$C_6$)-alkylsulfinyl, halo-($C_1$-$C_6$)-alkylsulfinyl, ($C_1$-$C_6$)-alkylsulfonyl, halo-($C_1$-$C_6$)-alkylsulfonyl, ($C_3$-$C_8$)-cycloalkylsulfonyl, ($C_1$-$C_6$)-alkylamino, di-($C_1$-$C_6$)-alkylamino, halo-($C_1$-$C_6$)-alkylamino, halodi-($C_1$-$C_8$)-alkylamino or ($C_3$-$C_8$)-cycloalkylamino, or two vicinal $R^6$ radicals form a ($C_3$-$C_6$)-alkylene group in which p carbon atoms are replaced by oxygen, sulfur or nitrogen, and in which one carbon atom bears t oxo groups, Y and Z are each independently O or S, $W^1$ is ($C_1$-$C_{10}$)-alkylene, ($C_2$-$C_6$)-alkenylene or ($C_2$-$C_6$)-alkynylene, $W^2$ is ($C_1$-$C_{10}$)-alkylene, G is heteroaryl or heterocyclyl, each of which is substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, where heterocyclyl bears n oxo groups, n is 0, 1 or 2, p is 0, 1, 2 or 3, s is 0, 1, 2, 3, 4 or 5, t is 0 or 1.

3. 1,2,4-Triazine-3,5-dione-6-carboxamide of formula (I) or salt thereof as claimed in claim 1, in which $R^1$ is $(C_1-C_{10})$-alkyl, $(C_2-C_{10})$-alkenyl, $(C_2-C_{10})$-alkynyl, halo-$(C_1-C_{10})$-alkyl, halo-$(C_2-C_{10})$-alkenyl, halo-$(C_2-C_{10})$-alkynyl, $(C_3-C_{10})$-cycloalkyl, halo-$(C_3-C_{10})$-cycloalkyl, $(C_1-C_4)$-alkyl-$(C_3-C_7)$-cycloalkyl, $(C_3-C_7)$-cycloalkyl-$(C_1-C_6)$-alkyl, $(C_3-C_7)$-cycloalkyl-$(C_3-C_7)$-cycloalkyl, halo-$(C_3-C_7)$-cycloalkyl-$(C_1-C_6)$-alkyl, $(C_1-C_6)$-alkyl-$(C_3-C_7)$-cycloalkyl-$(C_1-C_6)$-alkyl, $(C_3-C_{12})$-cycloalkenyl, halo-$(C_3-C_{12})$-cycloalkenyl, $(C_1-C_6)$-alkoxy-$(C_1-C_6)$-alkyl, $(C_1-C_6)$-alkoxy-$(C_2-C_6)$-alkenyl, $(C_1-C_6)$-alkyl-$(C_3-C_7)$-cycloalkyl, $(C_1-C_6)$-alkoxy-$(C_3-C_7)$-cycloalkyl, $(C_3-C_7)$-cycloalkoxy-$(C_1-C_6)$-alkyl, $(C_3-C_7)$-cycloalkoxy-$(C_1-C_6)$-alkoxy-$(C_1-C_6)$-alkyl, $(C_1-C_6)$-alkoxy-$(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkylamino-$(C_1-C_6)$-alkyl, di-$(C_1-C_6)$-alkylamino-$(C_1-C_6)$-alkyl, halo-$(C_1-C_6)$-alkylamino-$(C_1-C_6)$-alkyl, $(C_3-C_7)$-cycloalkylamino-$(C_1-C_6)$-alkyl, $(C_1-C_6)$-alkylcarbonyl, halo-$(C_1-C_6)$-alkylcarbonyl, $(C_3-C_7)$-cycloalkylcarbonyl, $(C_1-C_6)$-alkoxycarbonyl, $(C_3-C_7)$-cycloalkoxycarbonyl, $(C_3-C_7)$-cycloalkyl-$(C_1-C_6)$-alkoxycarbonyl, $(C_1-C_6)$-alkylaminocarbonyl, di-$(C_1-C_6)$-alkylaminocarbonyl, $(C_3-C_7)$-cycloalkylaminocarbonyl, cyano-$(C_1-C_6)$-alkyl, hydroxy-$(C_1-C_6)$-alkyl, $(C_3-C_7)$-cycloalkenyl-$(C_1-C_6)$-alkyl, halo-$(C_1-C_6)$-alkoxy-$(C_1-C_6)$-alkyl, $(C_1-C_6)$-alkoxyhalo-$(C_1-C_6)$-alkyl, halo-$(C_1-C_6)$-alkoxyhalo-$(C_1-C_6)$-alkyl, halo-$(C_3-C_7)$-cycloalkoxy-$(C_1-C_6)$-alkyl, $(C_3-C_7)$-cycloalkenyloxy-$(C_1-C_6)$-alkyl, halo-$(C_3-C_7)$-cycloalkenyloxy-$(C_1-C_6)$-alkyl, di-$(C_1-C_6)$-alkoxy-$(C_1-C_6)$-alkyl, $(C_1-C_6)$-alkoxy-$(C_1-C_6)$-alkylcarbonyl, $(C_1-C_6)$-alkoxycarbonyl-$(C_1-C_6)$-alkyl, halo-$(C_1-C_6)$-alkoxycarbonyl, $(C_1-C_{10})$-alkoxy, halo-$(C_1-C_{10})$-alkoxy, $(C_3-C_{12})$-cycloalkoxy, halo-$(C_3-C_7)$-cycloalkoxy, $(C_3-C_7)$-cycloalkyl-$(C_1-C_6)$-alkoxy, $(C_2-C_{12})$-alkenyloxy, halo-$(C_2-C_{10})$-alkenyloxy, $(C_2-C_{10})$-alkynyloxy, halo-$(C_3-C_{10})$-alkynyloxy, $(C_1-C_6)$-alkoxy-$(C_1-C_6)$-alkoxy, $(C_1-C_6)$-alkylcarbonyloxy, halo-$(C_2-C_{12})$-alkylcarbonyloxy, $(C_3-C_7)$-cycloalkylcarbonyloxy, $(C_1-C_6)$-alkylcarbonyl-$(C_1-C_6)$-alkoxy, $(C_1-C_{10})$-alkylthio, halo-$(C_1-C_{10})$-alkylthio, $(C_3-C_{12})$-cycloalkylthio, $(C_1-C_{10})$-alkylsulfinyl, halo-$(C_1-C_{10})$-alkylsulfinyl, $(C_1-C_{10})$-alkylsulfonyl, halo-$(C_1-C_{10})$-alkylsulfonyl, $(C_3-C_{12})$-cycloalkylsulfonyl, $(C_1-C_6)$-alkylcarbonylthio, $(C_1-C_6)$-alkyl(thiocarbonyl)thio, $(C_3-C_{12})$-cycloalkylsulfinyl, $(C_1-C_6)$-alkylaminosulfonyl, di-$(C_1-C_6)$-alkylaminosulfonyl, $(C_1-C_6)$-alkylamino, di-$(C_1-C_6)$-alkylamino, halo-$(C_1-C_6)$-alkylamino, halodi-$(C_1-C_6)$-alkylamino, $(C_3-C_{12})$-cycloalkylamino, $(C_1-C_6)$-alkylcarbonylamino, halo-$(C_1-C_6)$-alkylcarbonylamino, $(C_1-C_{10})$-alkylsulfonylamino, halo-$(C_1-C_{10})$-alkylsulfonylamino, $(C_3-C_7)$-cycloalkyl-$(C_1-C_6)$-alkylamino, cyano, hydroxyl, amino, C(=O)OH, C(=O)NHOH, $SO_2NH_2$, $SO_2NHCN$, $SO_2NHOH$, NHCHO, or $R^1$ is phenyl, $W^1$-(phenyl), where the phenyl rings each bear s $R^6$ substituents, or $R^1$ is G, $R^2$ is $(C_1-C_4)$-alkyl, $(C_1-C_4)$-haloalkyl, phenyl, heteroaryl, where the phenyl or heteroaryl rings in the two aforementioned radicals each bear s $R^6$ substituents, Q is a $Q^1$, $Q^2$, $Q^3$ or $Q^4$ radical,

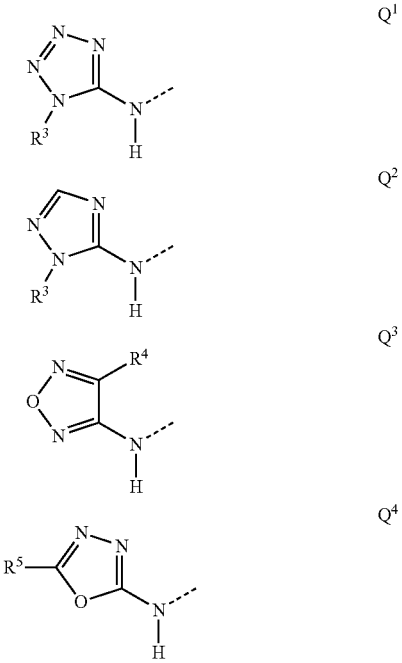

R is $(C_1-C_8)$-alkyl, $(C_2-C_8)$-alkenyl or $(C_2-C_8)$-alkynyl, each of which is substituted by s radicals from the group consisting of halogen, cyano, nitro, $S(O)_n$—$(C_1-C_6)$-alkyl, $(C_1-C_6)$-alkoxy and halo-$(C_1-C_6)$-alkoxy, $R^4$ is $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1H, 1-pyrazol-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl or piperidin-1-yl, or phenyl in each case substituted by s radicals from the group consisting of methyl, ethyl, methoxy, trifluoromethyl and halogen, $R^5$ is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, $R^6$ is halogen, cyano, nitro, $(C_1-C_6)$-alkyl, $(C_2-C_6)$-alkenyl, $(C_2-C_6)$-alkynyl, halo-$(C_1-C_6)$-alkyl, $(C_3-C_6)$-cycloalkyl, $(C_1-C_6)$-alkoxy, halo-$(C_1-C_6)$-alkoxy, $(C_1-C_6)$-alkylthio, $(C_1-C_6)$-alkylsulfinyl, $(C_1-C_6)$-alkylsulfonyl, phenyl, methylenedioxo, Y and Z are each independently O or S, $W^1$ is $(C_1-C_{10})$-alkylene, G is heteroaryl or heterocyclyl, each of which is substituted by s radicals from the group consisting of halogen, nitro, cyano, (C₁-C₆)-alkyl, halo-(C₁-C₃)-alkyl, cyclopropyl, $S(O)_n$—(C₁-C₃)-alkyl, (C₁-C₄)-alkoxy, halo-(C₁-C₄)-alkoxy and (C₁-C₄)-alkoxy-(C₁-C₄)-alkyl, where heterocyclyl bears n oxo groups, n is 0, 1 or 2, p is 0, 1, 2 or 3, s is 0, 1, 2, 3, 4 or 5.

4. A herbicidal composition comprising a herbicidally effective amount of one or more compounds of formula (I) or salt as claimed in claim 1.

5. The herbicidal composition as claimed in claim 4 in a mixture with one or more formulating auxiliaries.

6. The herbicidal composition as claimed in claim 4, comprising one or more further pesticidally active substances from the group consisting of insecticides, acaricides, herbicides, fungicides, safeners, and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 4, comprising a further herbicide.

10. A method for controlling unwanted plants, comprising applying an effective amount of one or more compounds of formula (I) or salts as claimed in claim 1 to one or more plants and/or to a site of unwanted plant growth.

11. The method as claimed in claim 10, wherein the effective amount of one or more compounds of formula (I) or salts is applied to one or more unwanted plants in one or more crops of useful plants.

12. The method as claimed in claim 11, wherein the useful plants are transgenic useful plants.

13. The 1,2,4-triazine-3,5-dione-6-carboxamide of formula (I) or salt thereof as claimed in claim 1, wherein Q is a Q¹ radical,

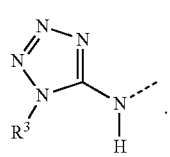

14. The 1,2,4-triazine-3,5-dione-6-carboxamide of formula (I) or salt thereof as claimed in claim 1, wherein Q is a Q² radical,

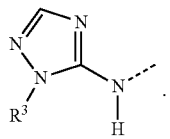

15. The 1,2,4-triazine-3,5-dione-6-carboxamide of formula (I) or salt thereof as claimed in claim 1, wherein Q is a Q³ radical,

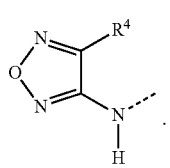

16. The 1,2,4-triazine-3,5-dione-6-carboxamide of formula (I) or salt thereof as claimed in claim 1, wherein Q is a Q⁴ radical,

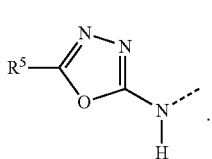

17. The 1,2,4-triazine-3,5-dione-6-carboxamide of formula (I) or salt thereof as claimed in claim 1, wherein
Y is O, and
Z is O.

18. The 1,2,4-triazine-3,5-dione-6-carboxamide of formula (I) or salt thereof as claimed in claim 17, wherein Q is a Q¹ radical,

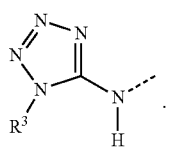

* * * * *